United States Patent
Slater, Jr.

(10) Patent No.: US 7,143,458 B2
(45) Date of Patent: Dec. 5, 2006

(54) STABILIZER FOR FOREARM TRACTION

(76) Inventor: Robert R. Slater, Jr., 2057 Boulder Mine Way, Gold River, CA (US) 95670

( * ) Notice: Subject to any disclaimer, the term of this patent is extended or adjusted under 35 U.S.C. 154(b) by 508 days.

(21) Appl. No.: 10/391,032

(22) Filed: Mar. 17, 2003

(65) Prior Publication Data
US 2004/0186404 A1     Sep. 23, 2004

(51) Int. Cl.
*A61G 13/00* (2006.01)

(52) U.S. Cl. ................. 5/623; 5/647; 128/845; 128/846

(58) Field of Classification Search ........... 602/36, 602/39, 40, 32–34, 35; 5/623, 621, 617, 5/646, 647, 630; 128/845, 846, 878
See application file for complete search history.

(56) References Cited

U.S. PATENT DOCUMENTS

| | | | | |
|---|---|---|---|---|
| 473,200 A * | 4/1892 | Streeter | ............ | 5/623 |
| 541,863 A | 7/1895 | Loomis | | |
| 988,923 A * | 4/1911 | Bauerfeind | ............ | 5/646 |
| 1,296,722 A * | 3/1919 | Washburn | ............ | 602/39 |
| 1,516,795 A * | 11/1924 | Schwarting | ............ | 5/646 |
| 2,119,325 A * | 5/1938 | Goodhart | ............ | 602/16 |
| 2,266,230 A | 12/1941 | Mazzeo et al. | | |
| 2,850,342 A | 9/1958 | Robinson | | |
| 3,540,719 A | 11/1970 | Romney et al. | | |
| 3,880,417 A * | 4/1975 | Burris et al. | ............ | 5/624 |
| 3,904,195 A * | 9/1975 | Chavanne | ............ | 482/142 |
| 4,054,282 A | 10/1977 | Hamer | | |
| 4,113,218 A * | 9/1978 | Linder | ............ | 248/291.1 |
| 4,252,306 A | 2/1981 | Johnson et al. | | |
| 4,355,631 A * | 10/1982 | LeVahn | ............ | 600/230 |
| 4,373,709 A | 2/1983 | Whitt | | |
| 4,428,571 A | 1/1984 | Sugarman | | |
| 4,628,911 A | 12/1986 | Bornstein | | |
| 4,742,981 A * | 5/1988 | Converse | ............ | 248/231.71 |
| 4,766,892 A * | 8/1988 | Kreitman | ............ | 5/623 |
| 4,772,002 A | 9/1988 | McConnell et al. | | |
| 4,930,523 A * | 6/1990 | Laico et al. | ............ | 5/87.1 |
| 4,996,977 A * | 3/1991 | Tiedeken | ............ | 128/878 |
| 5,085,658 A | 2/1992 | Meyer | | |
| 5,156,168 A | 10/1992 | Canterna | | |
| 5,372,145 A * | 12/1994 | Berger | ............ | 128/878 |
| 5,881,730 A * | 3/1999 | Burger | ............ | 128/878 |
| 6,298,507 B1 * | 10/2001 | Clyburn | ............ | 5/623 |
| 6,368,271 B1 * | 4/2002 | Sharratt | ............ | 600/228 |
| 6,467,487 B1 | 10/2002 | Rios | | |
| 6,820,621 B1 * | 11/2004 | DeMayo | ............ | 128/845 |
| 6,932,783 B1 * | 8/2005 | Donato | ............ | 602/36 |
| 6,941,951 B1 * | 9/2005 | Hubert et al. | ............ | 128/845 |
| 2002/0007188 A1 * | 1/2002 | Arambula et al. | ............ | 606/130 |

* cited by examiner

*Primary Examiner*—Henry Bennett
*Assistant Examiner*—Huong Q. Pham
(74) *Attorney, Agent, or Firm*—M. Henry Heines; Townsend and Townsend and Crew LLP.

(57) ABSTRACT

The arm of a patient undergoing wrist arthroscopy or other procedures that involve traction on the forearm, wrist or hand in a vertical position is immobilized in a device containing a stabilizing arch that can be readily secured to an arm board. The device offers multiple degrees of freedom to accommodate arm boards of different widths and heights, and secures the arm of the patient without attaching anything to the arm that might affect the circulation to the involved extremity.

8 Claims, 2 Drawing Sheets

STABILIZER FOR FOREARM TRACTION

BACKGROUND OF THE INVENTION

1. Field of the Invention

This invention is in the field of clinical procedures involving the wrist and upper extremity, with particular application to wrist arthroscopy and to methods and devices for applying traction to the hand and wrist.

2. Description of the Prior Art

Wrist arthroscopy is a surgical technique of increasing popularity due to the fact that it is only minimally invasive and affords a thorough and accurate means of diagnosing and treating disorders of the wrist. Diagnostic arthroscopy enables the physician to evaluate the wrist joint to determine whether a problem exists and to identify the nature of the problem, while with corrective arthroscopy the physician can both identify the problem and perform the procedure or procedures necessary to treat or eliminate the problem. Among the various types of problems that can be evaluated and in many cases corrected by wrist arthroscopy are sources of chronic wrist pain, the presence of bone fragments and debris resulting from a fracture, the misalignment of bone pieces broken in a fracture, the presence of growths between wrist bones called ganglion cysts, the presence of torn ligaments or tears in the triangular fibrocartilage complex, and synovitis or inflammation of the lining of the wrist joint. In the typical arthroscopic procedure, the surgeon makes small incisions in the wrist and inserts an arthroscope, which is a small instrument containing a lens, a miniature camera, and a lighting system. The arthroscope produces three-dimensional images that are viewed on a television monitor, allowing the surgeon to accurately identify the cause of the problem so that appropriate corrective action can be taken. Surgical tools such as probes, forceps, knives, radiofrequency devices or electrocoagulation devices can then be inserted to correct the problem while the arthroscope is still in place. In addition to its use on the wrist, arthroscopy can be used on smaller joints as well, such as those in the hand.

To perform arthroscopy, the surgeon must stabilize the hand and upper extremity so that traction can be applied. With the patient lying on a hospital bed, the upper extremity is typically extended outward from the patient's body and bent 90° at the elbow so that the forearm is perpendicular to the floor with the hand pointed upward toward the ceiling. Traction is achieved by applying an upward force to the fingers through mesh finger traps that are attached to a tower. The tower is arranged to allow the traps to be moved up and down to control the tension being applied to the joints in the wrist and hand. The tension is closely controlled so that the amount applied is sufficient to open the joint spaces so that the surgeon can insert the tools and instruments safely, and once they are inserted, manipulate them to perform the desired functions effectively. The instruments can then be withdrawn at the end of the procedure without inflicting damage to the joint. The application of tension requires an upward force on the finger traps together with a stabilizing force at the elbow. The stabilizing force must not be so constrictive that it causes discomfort to the patient or affects circulation to the extremity being treated. Other considerations are the need for the surgeon to have access to surgical tools and equipment that are typically used during surgical procedures in general, as well as the ability to perform these functions without requiring an operating table of specialized design.

These and other concerns are addressed by the present invention.

SUMMARY OF THE INVENTION

The present invention resides in an arm stabilizing device that holds the upper arm down as the fingers or hand are pulled upward to apply traction through the wrist. The device is mountable to an operating room table and contains multiple degrees of freedom for adjustment to patient bodies of different sizes and operating room tables of any width or height. Despite this adjustability, the device provides a secure anchoring effect that avoids slippage of the arm without being fastened to or encircling the patient's arm. With such versatility and flexibility, the device is inexpensive to construct, simple to use, and usable with a wide variety of existing operating tables and surgical equipment.

Among the features of the device that enable it to serve these purposes are a frame of variable height with a crossbar of variable width, an arch or C-shaped restraining member that extends below the crossbar and opens downward to engage the upper arm of the patient, and various clamping components to fix the width of the frame and the height of the crossbar.

These and other features, objects, and advantages of the invention will be apparent from the description that follows.

DETAILED DESCRIPTION OF THE INVENTION AND PREFERRED EMBODIMENTS

Figure 1:
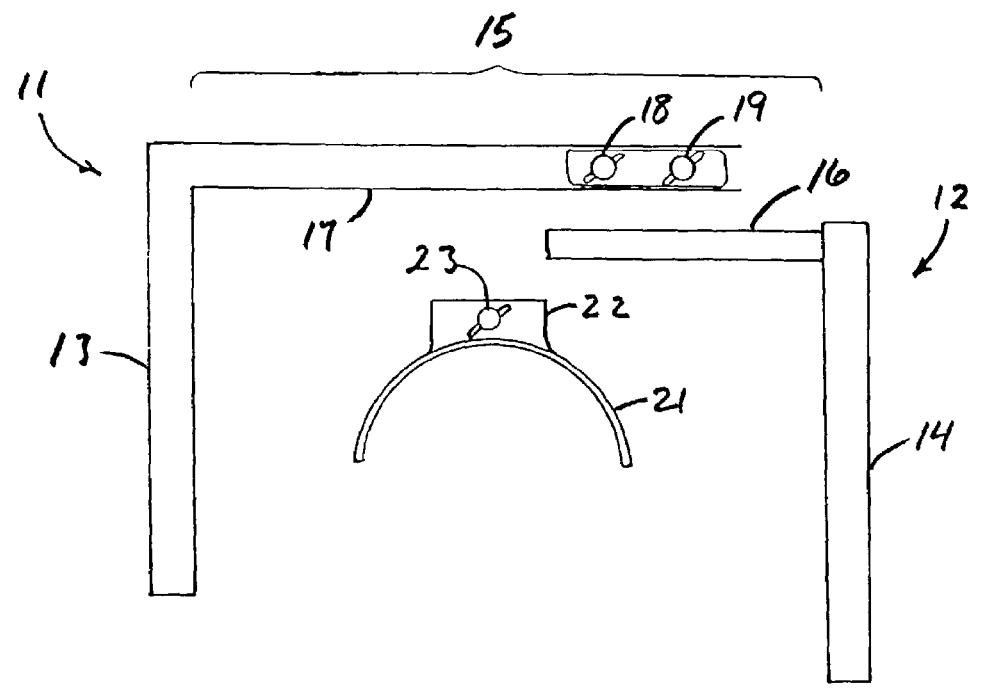
FIG. 1 is a plan view of individual components of one example of a stabilizing device in accordance with the present invention, arranged to show how the components fit together.
Figure 1:

While the present invention can vary in shape, configuration and component parts, a full understanding of the concepts and principles of the invention can be gained by a detailed review of one illustrative embodiment. Such an embodiment is shown in the drawings.

The components of this embodiment are shown separated from each other in FIG. 1. These components include a frame consisting of two parts 11, 12 which are joined together in use but shown individually for clarity. The two parts form vertical supports 13, 14 and a crossbar 15 spanning the gap between the two vertical supports. The crossbar 15 is formed from a rod 16 on one of the two parts 12 and a sleeve 17 on the other 11. The sleeve 17 is sufficiently large to receive the rod 16 and to allow the rod to slide inside the sleeve to change the length of the crossbar 15. Two tightening screws 18, 19 which can be manually operated pass through the wall of the sleeve 17 to engage and seize the rod 16, thereby fixing the position of the rod within the sleeve and hence the length of the crossbar. In this manner, the distance between the vertical supports 13, 14 can be adjusted and fixed over a range of distances determined by the length of the crossbar rod 16, the length of the crossbar sleeve 17, and the positions of the crossbar screws 18, 19 on the sleeve.

While a single screw might suffice, two screws 18, 19 are shown in the Figure. Two or more screws may provide a greater range of variability and a more rigid fixation of the crossbar length. Any other known mechanical device that is capable of seizing two parts together can be used in place of the screw, and these alternatives will be readily apparent to those skilled in the design and manufacture of mechanical components. Examples of these alternatives are spring-biased joining members, quick-connect joints, and any components that are joined in either sliding or rolling contact with seizing members, stops, or brakes. The length variation may be either a continuous range as in the embodiment shown or a series of discrete lengths. Different lengths can be established for example by a pin and holes, i.e., the inner rod 16 can have a row of holes arranged lengthwise to receive a spring-loaded pin mounted to the sleeve 17.

The crossbar rod 16 is preferably non-circular in cross section, and the cross section of the crossbar sleeve 17 is preferably of the same shape of the rod although large enough that the rod can slide through the sleeve. The non-circular shape is preferred for purposes of preventing the two parts from rotating relative to each other and thus keeping the vertical supports 13, 14 approximately parallel. In a currently preferred construction, the cross sections are rectangular and, most preferably, approximately square.

A further component shown in FIG. 1 is the arch or C-shaped restraining member 21. The arch can be of any curvature, and either of a constant radius or a variable radius. A convenient curvature is an arc of a circle, extending half or less of the circumference of the circle. The arch 21 is parallel to the crossbar 15 and opens downward so that the arch can be lowered onto the patient's arm to prepare the patient for the arthroscopic procedure, and lifted from the patient's arm after the procedure is completed. When the arch is an arc of a circle, the diameter is not critical provided that the diameter is large enough to accommodate the patient's arm and small enough that the arm will not slip from the center of the arc during the procedure. In most cases, a diameter of at least about 10 cm, and preferably from about 15 cm to about 50 cm will provide the best results.

Attachment of the arch 21 to the crossbar 15 is achieved by a mounting bracket 22 that fits over the crossbar sleeve 17 and is secured to the crossbar sleeve by compression using a tightening screw 23. Here as well, any releasable securement device can be used in place of the screw. Examples are a pin, possibly spring-mounted, to mate with a hole in the crossbar sleeve and a spring-mounted clamp. Other examples will be readily apparent to those skilled in the art. The mounting bracket 22 shown in the Figure consists of two plates extending upward from the arch, forming a trough into which the crossbar sleeve can be inserted, with the tightening screw threaded through one of the two plates. As an alternative to the two plates, the mounting bracket can itself be a sleeve through which the crossbar is inserted.

The securement of the frame and arch to an operating table in a manner that provides the surgeon with the ability to adjust the height of the arch is achieved by a pair of clamps 24, 25. The two clamps in this embodiment are identical, and each is a composite clamp with two clamping components, one that determines the height of the frame and one that secures the frame to the operating table. Preferably, the two clamping components are independently operable, and it is also preferred that they be manually operable.

Examining the left clamp 24 in detail, the body 26 of the clamp is a sleeve that receives the left vertical support 13. By virtue of this sleeve construction, the clamp 24 can be placed at any height on the vertical support 13 thereby securing the crossbar 15 at any height above the table to which the device is attached. Once the height is selected, the position of the clamp on the vertical support 13 is fixed by compression, using a manually operated tightening screw 27. The range of positions is continuous in this embodiment, but as described above in connection with the two parts of the crossbar, alternate connections can be used that would provide a series of discrete positions. The tightening screw itself can be replaced by any of a variety of alternatives such as those listed above, all known to those skilled in the art.

The second clamping component of the clamp 24, which secures the clamp to the operating table, is a pair of horizontal plates 31, 32 with a gap between them to receive the edge of the table. A manually operated tightening screw 33 secures the clamp position on the table. As in the case of the other clamping components, this tightening screw can be replaced by any number of alternatives known to those skilled in the art, including spring-loaded clamps.

Figure 2:
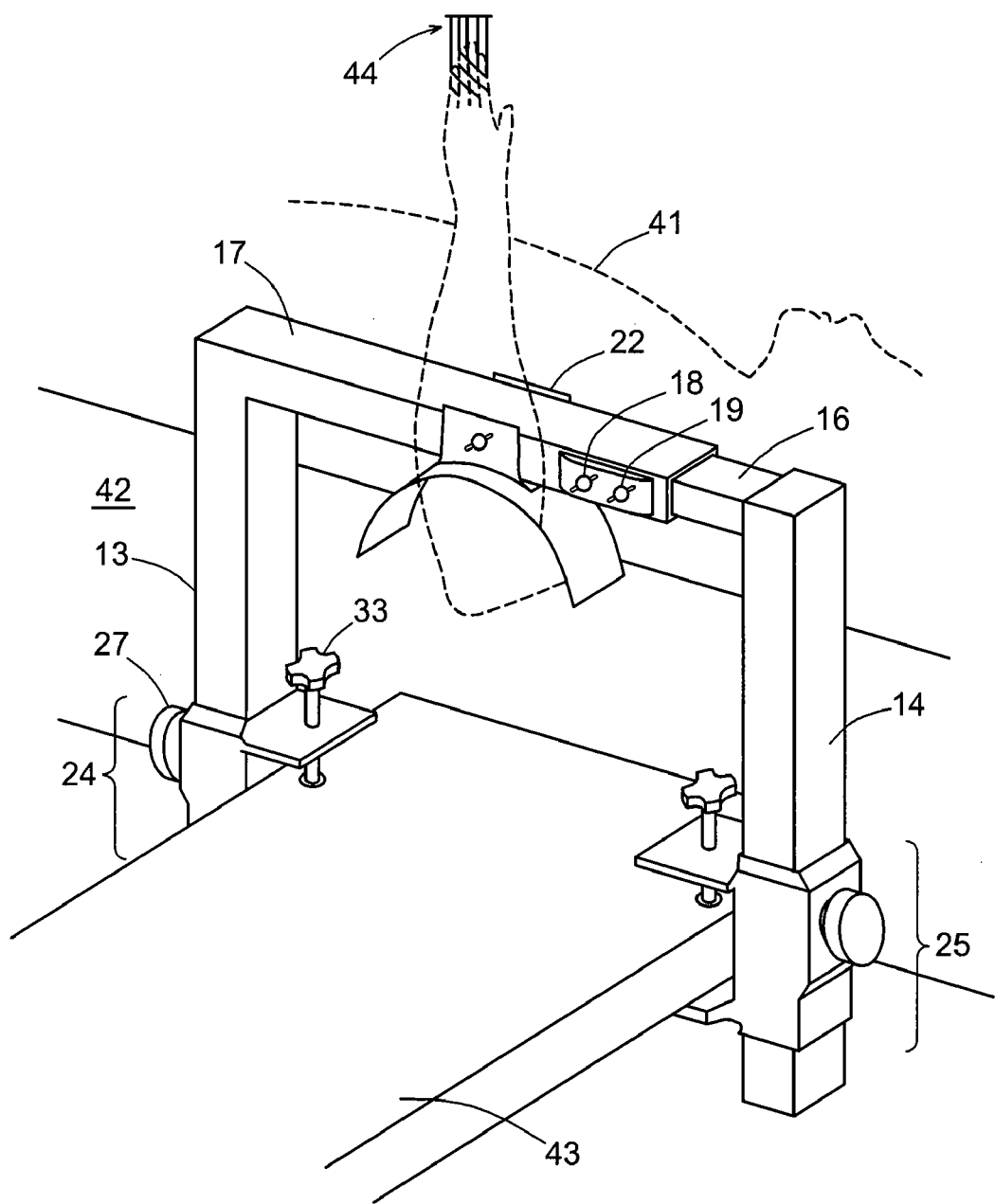
FIG. 2 is a perspective view of the stabilizing device whose components are shown in FIG. 1, fully assembled and in use on a patient to whom traction is being applied.

The components shown in FIG. 1 are shown in assembled form in FIG. 2 in use with a patient. This view shows the patient 41 in dashed lines lying on his or her back on a bed 42, with an arm board 43 beside the bed to support the upper extremity. The frame is secured to the arm board 43 by the clamps 24, 25, and the height of the frame is adjusted by the clamps 24, 25 such that the arch 21 contacts the arm of the patient. No part of the device as a whole contacts the underside of the patient's wrist, which is instead supported by the arm board 43, which is lowered in this view for visibility. Tension is applied to the patient's wrist by pulling upwards on the patient's fingers. This is accomplished by conventional methods, a notable example of which is the use of finger traps 44 attached to a traction tower (not shown). These components are readily apparent from surgical equipment suppliers such as Linvatec Corporation (Utica, N.Y., USA.)

The foregoing descriptions are offered primarily for purposes of illustration. Further variations and modifications that still embody the basic elements of this invention will be readily apparent to those skilled in the art and are included within the scope of this invention.

What is claimed is:

1. An arm stabilizing device for use in surgical procedures on the wrist, said device comprising:
   a frame comprising a pair of vertical supports separated by a gap and supporting a crossbar of variable length spanning said gap;
   crossbar clamping means for fixing the length of said crossbar at a selected length;
   vertical support clamping means for securing said vertical supports to a table and for varying the height of said crossbar above said table; and
   a C-shaped restraining member mounted to said crossbar in a downwardly opening direction and parallel to said crossbar.

2. An arm stabilizing device in accordance with claim 1 in which said C-shaped restraining member is an arc of a circle having a diameter of at least about 10 cm.

3. An arm stabilizing device in accordance with claim 1 in which said C-shaped restraining member is an arc of a circle having a diameter of from about 15 cm to about 50 cm.

4. An arm stabilizing device in accordance with claim 1 in which said crossbar is comprised of a non-circular rod and a sleeve slidable over said rod, and said crossbar clamping means are means for immobilizing said sleeve relative to said non-circular rod.

5. An arm stabilizing device in accordance with claim 1 in which said C-shaped restraining member is mounted to said crossbar by a movable mounting permitting movement of said C shaped restraining member along the length of said crossbar.

6. An arm stabilizing device in accordance with claim 1 in which said vertical support clamping means consists of a pair of composite clamps, each composite clamp comprising a sleeve slidable over one of said vertical supports, a first compressing member to fix said sleeve at a selected position along said vertical support, and a second compressing member to grasp an edge of a table thereby anchoring said device to said table.

7. An arm stabilizing device in accordance with claim 6 in which said first and second compressing members are independently controlled by manually operable handles.

8. An arm stabilizing device in accordance with claim 1 in which said vertical support clamping means secures said vertical supports to a table edge.

* * * * *